United States Patent [19]

Hamer et al.

[11] 4,442,205

[45] Apr. 10, 1984

[54] SIMIAN VIRUS RECOMBINANT THAT DIRECTS THE SYNTHESIS OF HEPATITIS B SURFACE ANTIGEN

[75] Inventors: Dean H. Hamer, Washington, D.C.; John Gerin, Bethesda, Md.

[73] Assignee: The United States of America as represented by the Department of Health and Human Services, Washington, D.C.

[21] Appl. No.: 304,571

[22] Filed: Sep. 22, 1981

[51] Int. Cl.$^3$ .................. C12P 21/00; C12N 15/00; C12N 1/00; C12N 7/06
[52] U.S. Cl. ....................... 435/68; 435/172; 435/317; 435/238; 424/89
[58] Field of Search ............ 435/172, 68, 317, 238, 435/70, 71

[56] References Cited

PUBLICATIONS

Moriority et al, PNAS USA vol. 78, pp. 2606–2610, Apr. 1981.
Burnell et al, Nature, vol. 279, pp. 43–47 (May 1979).
Dubois et al, Proc. Natl. Acad. Sci. USA vol. 77, No. 8, pp. 4549–4553 (Aug. 1980).
Charnay et al, Nature, vol. 286, pp. 893–895 (Aug. 1980).
Sninsky et al, Nature, vol. 279, pp. 346–348 (May 1979).
Valenzuela et al, Nature, vol. 280, pp. 815–819 (1979).
Mulligan et al, Nature, vol. 277, pp. 108–114 (Jan. 1979).
Goff et al, J. Mol. Biol., vol. 133, pp. 359–383 (1979).

Primary Examiner—Alvin E. Tanenholtz
Attorney, Agent, or Firm—John S. Roberts, Jr.

[57] ABSTRACT

A process for producing a recombinant between simian virus 40 (SV40) and hepatitis B virus (HBV) is given. When tissue culture cells are infected with the recombinant, hepatitis B surface antigen is produced. Because a single cloned gene is used, the surface antigen produced is homogeneous and can be produced without conventional dependence on human sera. The antigen is excreted into the culture medium as 22 nm particles with the same physical properties, antigenic composition and constituent polypeptides as those found in the sera of patients with Type B hepatitis. The antigen is useful for the preparation of vaccines.

2 Claims, No Drawings

SIMIAN VIRUS RECOMBINANT THAT DIRECTS THE SYNTHESIS OF HEPATITIS B SURFACE ANTIGEN

STATEMENT OF PRIOR ART

DuBois et al, "Excretion of hepatitis B surface antigen particles from mouse cells transformed with cloned viral DNA," *Proc. Natl. Acad. Sci.*, Vol. 77, No. 8, pp. 4549-4553, August, 1980. The surface antigen is excreted into the cell culture medium when a plasmid with two cloned hepatitis B viral genomes is introduced into mouse cells using cotransformation. No SV40 vector is used in this procedure. Moreover, in these experiments HBsAg expression depended upon the presence of two complete, tandem copies of the HBV genome rather than upon a defined subfragment.

Charnay et al, "Biosynthesis of hepatitis B virus surface antigen in *E. coli*," *Nature*, Vol. 286, August, 1980. This hybrid antigen is neither glycosylated, assembled into particles, nor excreted from the bacterial host.

Conventional preparations of hepatitis B surface antigen are given, for example, in U.S. Pat. Nos. 4,113,712; 4,118,479; 4,138,287 and 4,186,193.

STATEMENT OF DEPOSIT

SV40 vector cleaved with BamHI at 0.14 map units and EcoRI at 0.00 map units and designated Y182 has been filed with the American Type Culture Collection and received ATCC Number 31964.

BACKGROUND

At least half of the world population shows evidence for past or present infection by hepatitis B virus (HBV), and the approximately 200 million carriers in the world today are at serious risk to chronic liver disease and, possibly, primary liver cancer. The classic marker for chronic infection by this virus is the surface antigen, HBsAg, which circulates in the serum of HBV carriers in three morphological forms: 22 nm spherical particles, 22 nm filaments of various lengths and the 42 nm spherical form known as the Dane particle. The 22 nm particles and filaments are subviral forms containing two predominant polypeptides, with apparent molecular weights of about 23,000 and 29,000, together with several minor polypeptides of larger size. The two predominant species, which are probably identical except that the larger is glycosylated, carry both the group (a) and the subtype (d/y) antigenic determinants of HBsAg. The Dane particle, which represents the infectious virion, consists of a lipoprotein coat (HBsAg) surrounding an internal core particle which contains a DNA polymerase and the 3200 base pair (bp) circular DNA genome. The 22 nm particle is the predominant form in the sera of chronic carriers and circulates at concentrations as high as 100-200 µg/ml.

Characterization of the life cycle and biology of HBV has been hampered by its narrow host range, which is restricted to humans and a few other primates, and by its inability to grow in cultured cells. Problems associated with conventional purification and isolation from human serum are discussed, for example, in U.S. Pat. Nos. 4,113,712; 4,138,287 and 4,186,193.

Recently, however, several groups have succeeded in cloning the viral genome in *Escherichia coli* phage lambda (Charnay et al, Proc. Natl. Acad. Sci. USA 76, 2222-2226, 1979) and plasmid vector (Burrell et al, Nature 279, 43-47, 1979, and Sninsky et al, Nature 279, 346-348, 1979) and in determining its primary structure (Valenzuela et al, Nature 280, 815-819, 1979; Pasek et al, Nature 282, 575-579, 1979; and Galibert et al, Nature 281, 646-650, 1979). This has allowed the identification of a continuous 892 bp sequence that could encode surface antigen, a 549 bp sequence that may specify the core antigen and several additional open sequences of unknown function.

Although the DNA sequence provides crucial structural information, it clearly is not sufficient to establish all of the HBV gene products nor to understand how these products interact during infection of the target cell. For this purpose it would be useful to develop a system for introducing defined portions of the viral genome into cultured cells. Simian virus 40 (SV40), a small DNA tumor virus that can lytically infect cultured monkey cells, provides a useful vector for this purpose. The present invention provides for the construction and propagation of an SV40 recombinant carrying a 1350 bp fragment of HBV DNA that includes the structural sequences for surface antigen. Monkey kidney cells infected with this recombinant synthesize surface antigen that is excreted into the culture media as 22 nm particles. These results set an upper limit on the amount of HBV genetic information required for 22 nm particle formation and demonstrate the feasibility of using SV40 recombinants to study HBV gene expression in cultured primate cells. Ultimately, the antigen is useful in the preparation of vaccines, as a standard antigen reagent for testing hepatitis B surface antigen and antibody and as an antigen for immunizing animals to obtain a highly specific and strong antibody. Because the antigen is derived from a single cloned gene, it is homogeneous. Moreover, this unique process is free of contaminating serum components that conventional human serum processing cannot avoid.

SUMMARY OF THE INVENTION

Hepatitis B surface antigen is produced by amplifying the hepatitis B virus genome containing the hepatitis B surface antigen coding sequence by cloning the HBV genome in a plasmid, preparing an SV40 vector and ligating the HBV genome to the SV40 vector plasmid to produce a double recombinant HBV-SV40 plasmid, and transfecting the double recombinant in monkey kidney cells with helper virus and thereby producing hepatitis B surface antigen.

An SV40-HBV recombinant is constructed that retains about 70% of the SV40 genome and 40% of the HBV genome. This hybrid virus is replicated and packaged into SV40 virions in cultured monkey kidney cells, the permissive host for SV40, that have been coinfected with a complementing SV40 helper virus. The expression of the inserted HBV sequences was examined by both immunological and biochemical techniques. This showed that the recombinant directs the synthesis of surface antigen but no other known HBV-specific antigens. Furthermore, blocking assays and immunoprecipitation with monospecific antibodies demonstrated that the SVHBV (complex mixture of virus)-derived HBsAg had the same subtype (ad) as the antigen from the original donor of the HBV DNA. These observations demonstrate that both group and subtype-specific determinants of HBsAg are encoded within a limited portion of the viral genome.

The HBsAg encoded by SVHBV is excreted into the culture medium as 22 nm particles with the same buoyant density, sedimentation properties and morphology as the particles from human serum. These particles are produced at a rate of 2.5 μg/$10^7$ cells/2 days or approximately 3×$10^4$ particles/infected cell/day. This compares favorably with HBsAg production by the Alexander cell line derived from a human hepatocellular carcinoma. It is concluded that monkey kidney cells possess all of the functions required for particle formation and that the failure of HBV to grow in tissue culture is not due to a block at this stage of the viral life cycle.

The ability to propagate defined portions of the HBV genome in cultured primate cells raises several interesting experimental opportunities. In addition to the obvious possibility of vaccine production, it should be feasible to construct viruses that encode useful diagnostic reagents such as surface antigen peptides bearing single, highly specific immunological determinants. SV40-HBV hybrids might also be useful for identifying new HBV gene products; e.g., non-structural proteins that are not excreted into the serum. Finally, the availability of SV40-HBV recombinants provides an experimental system to investigate various mechanisms for the persistence and pathogenicity of HBV in liver cells.

DETAILS OF INVENTION

Materials and Methods:

The following methods have been described: general procedures for the construction of recombinant plasmids and viruses (Hamer, D. H. (1980) in *Genetic Engineering*, eds. Setlow & Hollander, Plenum Publishing Corp., New York, pp. 83-107); growth of African green monkey kidney cells and propagation of virus stocks (Hamer et al (1977), *J. Mol. Biol.*, 112, 155-182); preparation of plasmid (Clewell et al (1969), *Proc. Natl. Acad. Sci. USA*, 62, 1159-1166); and intracellular SV40 DNA (Hirt, *J. Mol. Biol.*, 26, 365-369); analysis of DNA by restriction endonuclease cleavage (Hamer et al (1977), *J. Mol. Biol.*, 112, 155-182) and agarose gel electrophoresis (Hayward et al (1972), *J. Mol. Biol.* 63, 383-395, and Cummings et al (1980), *Proc. Natl. Acad. Sci. USA*, 77, 1842-1846); and transformation of EK2 *E. coli* strain HB 101 (Cohen et al (1972), *Proc. Natl. Acad. Sci. USA*, 69, 2110-2114).

Restriction endonucleases and T4 DNA ligase were purchased from Bethesda Research Laboratories (Bethesda, MD) and reaction conditions were according to the supplier.

The source of HBV DNA was plasma, subtype adw, from an HBsAg-positive donor. Dane particles were purified by the method of Robinson (Robinson (1975), *Am. J. Med. Sci.*, 270, 151-159), incubated in the endogenous DNA polymerase reaction (Kaplan et al (1973), *J. Virol.*, 12, 995-1005) with all four deoxynucleotide triphosphates prior to DNA extraction.

The 22 nm form of HBsAg was purified from the plasma of chronic carriers as described previously (Gerin et al (1975), *J. Immunol.* 115, 100-105).

Hyperimmune guinea pig antiserum to HBsAg/ad was that supplied by the Research Resources Branch, NIAID (#V801-502-058) and monospecific antibodies to the HBs/a and HBs/d determinants were prepared from this serum by affinity chromatography (Shih et al (1978) *J. Immunol.*, 120, 520-525). Fluorescein isothiocyanate conjugated rabbit anti-guinea pig IgG was obtained from Cappel Laboratories (Cockranville, PA). Radioimmunoassays for hepatitis B core antigen (Purcell et al (1973/1974) *Intervirology*, 2, 231-243) delta antigen (Rizzetto et al (1980), *J. Immunol.*, 125, 318-324) and e antigen (HBeAg test kit, Abbott Laboratories (N. Chicago, IL) have been described. HBsAg was detected by the Ausria II radioimmunoassay (Abbott Laboratories) and quantitated by a parallel-line assay using a known standard (BoB HBsAg/adw vaccine, Reference Lot 1, 40 μg/ml). The d/y subtype of HBsAg was determined by the competition radioimmunoassay method of Hoofnagle (Hoofnagle et al, *Gastroenterology*, 72, 290-296).

Construction and Progapation of the SV40-HBV Recombinant

The SV40-HBV recombinant described here carried a 1350 bp fragment of HBV DNA, representing about 40% of the HBV genome, inserted into the late gene region of SV40. The first step in the construction of this recombinant was to amplify the HBV genome by cloning it in an *E. coli* plasmid vector. Dane particles were purified from the serum of a chronic HBsAg carrier, subtype adw, and the partially single-stranded viral genome was repaired by an endogenous DNA polymerase reaction. Two fragments of sizes 1350 and 1850 bp were obtained after cleavage of this DNA with Bam HI. Partial digestion with Bam HI generated a full HBV genome which was ligated to Bam HI-cleaved plasmid pBR322 DNA then cloned in *E. coli*.

From the published sequence data, it is anticipated that the HBsAg coding sequence would be located within the 1350 bp Bam HI fragment. This fragment was purified, ligated to a Bam HI-cleaved pBR322-SV40 vector plasmid and cloned in *E. coli*.

The SV40 vector is SV40 DNA cleaved with Bam HI at 0.14 map units and Eco RI at 0.00 map units. The fragment extending clockwise from the Bam site to the EcoRI site is cloned into plasmid pBR322 between a single Bam site and a single EcoRI site. Map units and orientation are based on the standard SV40 map where the EcoRI site is designated as map position 0. The direction clockwise is the same direction as late transcription.

Details of other recombinant DNA and SV40 genomes which are cloned and propagated in bacteria are given in copending application Ser. No. 309,110 filed Oct. 6, 1981. The advantages of this method are given and the expression of other proteins by the recombinant in eukaryotic cells by transformation or transfection is illustrated.

Digestion of the resultant pBR322-SV40-HBV "double recombinant" plasmid with Hae II removed all but 143 bp of the pBR322 DNA and yielded a homogenous preparation of 4950 bp SV40-HBV linear recombinant molecules. These molecules retain the SV40 origin of DNA replication and the complete SV40 early gene region but lack most of the SV40 late gene region and hence are defective. Nevertheless, they could be packaged into SV40 coats and propagated as virions by making a mixed DNA infection of monkey kidney cells with an SV40 temperature-sensitive early gene mutant (SV40ts$A_{239}$) as helper. This mixed infection was performed at the non-permissive temperature (39° C.) to insure that progeny virions would be produced only by cells doubly infected with the SV40-HBV recombinant, which supplies functional SV40 early gene products, and with the helper, which supplies all of the required SV40 late gene products.

To determine if the SV40-HBV recombinant was encapsidated into SV40 virions, it was acknowledged that only those genomes incorporated into viral particles during the original DNA infection would be transferred and replicated in a subsequent viral infection. Accordingly, a fresh culture of monkey cells was infected with the virus stock from the DNA infection, intracellular viral DNA was prepared three days later and examined by restriction endonuclease cleavage and agarose gel electrophoresis. This showed that the stock contained approximately 75% helper genomes and 5% SV40-HBV recombinant genomes retaining the complete 1350 bp HBV fragment. The remaining 20% of the DNA was found in a heterogenous collection of genomes with lengths ranging from about 3000 to 4900 base pairs. Although the structure of these molecules were not examined in detail, they may have arisen due to illegitimate intramolecular recombination of the linear DNA used for infection. This complex mixture of virus is referred to as SVHBV.

Monkey Kidney Cells Infected with SVHBV Synthesize HBsAg

Specific immunological assays were used to show that monkey kidney cells infected with SVHBV synthesized HBsAg but no other established HBV antigens. Immunofluorescence analysis revealed that approximately 45% of the cells infected with SVHBV expressed cytoplasmic HBsAg by 72 hours post infection, whereas uninfected and wild-type SV40 infected controls were negative. Quantitative radioimmunoassays showed that a culture of $2 \times 10^7$ cells produced a total of 2.5 µg of HBsAg. Of this, 40% was found in the medium and 60% was released from the cells by freeze-thawing and sonication. Subtype analysis showed that SVHBV-HBsAg had the same antigenic composition (d+, y−) as the antigen from the original donor of the HBV DNA. SVHBV infected cells were negative for HBcAg and δ antigen by immunofluorescence. The culture medium was negative (less than 2.1 P/N) for HBcAg, HBeAg and δ antigen by solid phase radioimmunoassay.

The HBsAg is Secreted from Monkey Kidney Cells as a Particle

SVHBV-HBsAg found in the tissue culture fluid is a 22 nm particle whose physical characteristics are those of the particles found in human serum. Isopycnic banding in CsCl of SVHBV-HBsAg revealed a buoyant density value (1.2 g/cm$^3$) identical to purified HBsAg run in parallel. The SVHBV-HBsAg material was further characterized by rate zonal centrifugation. Most of the SVHBV-specific antigen sedimented as a particle indistinguishable from the 22 nm particles found in human era. The morphology of the antigen was examined by electron microscopy of the pooled, concentrated peak fractions from the sucrose gradient. This revealed 22 nm spherical particles with the same appearance as the predominant form of HBsAg from human sera. Examination of the less highly purified material from the CsCl gradient also showed 22 nm filaments of variable lengths. No Dane particles were observed.

HBsAg Polypeptides

The polypeptide composition of the excreted SVHBV-HBsAg was analyzed by immunoprecipitation and gel electrophoresis of both chemically and biosynthetically labelled antigen. SVHBV-HBsAg from the rate sedimentation step was radioiodinated, resedimented, and immunoprecipitated by anti-HBs serum and antibodies against the group (a) and d-subtype specific determinants (Table 1 ).

TABLE 1

Immunoprecipitation of $^{125}$I-HBsAg from SVHBV-Infected Cells

| Sample | % Precipitation by Antiserum | | | |
|---|---|---|---|---|
| | Pre | -HBs/ad | -HBs/a | -HBs/d |
| Serum HBsAg/ad | 1.2 | 83.5 | 76.6 | 82.8 |
| SVHBV-HBsAg | 5.9 | 64.1 | 62.2 | 59.1 |

The peak fractions, 300 μl each, were pooled and concentrated 15-fold by pelleting. The concentrate was iodinated by the chloramine-T procedure and further purified by rate zonal centrifugatio in sucrose. A standard HBsAg/ad preparation isolated from human serum was iodinated and purified in parallel. Radioiodinated SVHBV-HBsAg and HBsAg/ad, 100 μl each, were incubated with 10 μl of guinea pig antisera at room temperature for 2 hr and precipitated with rabbit anti-guinea pig IgG, 140 μl, in 0.05% Tween 20/PBS. After further incubation at 4° C. for 18 hr, the mixture was centrifuged at 2300 xg for 30 min. and the precipitates were washed twice with 30 μl Tween-20/PBS. The supernatants were pooled and the percent precipitation was calculated.

Greater than 60% of the iodinated antigen was precipitated by anti-HBs and by both of the monospecific antibodies. SDS-gel electrophoresis of the denatured and reduced precipitates revealed two predominant polypeptides (P-1 and P-2) with the same mobilities as those isolated from human serum. These proteins are thought to be identical except that P2 is glycosylated. In addition, the iodinated SVHBV-HBsAg contained at least one of the minor polypeptides of higher molecular weight (P-5).

In a companion experiment, SVHBV-specific proteins were biosynthetically labelled by incubating the infected cells with $^{35}$S-methionine for 4 hours late in the lytic cycle. Direct examination of the medium from SVHBV infected cells revealed two proteins with the same mobilities as P-1 and P-2, both of which were precipitated by anti-HBs serum. In contrast, no such proteins were found in the media from uninfected or wildtype SV40 infected cells. This experiment also demonstrated that HBsAg is actively excreted rather than merely released by cell lysis because only a restricted subpopulation of the total cell proteins was found in the media.

We claim:

1. A process for producing hepatitis B surface antigen comprising the steps of:

(a) digesting HBV DNA and an *E. coli* plasmid with Bam HI and ligating the digest to produce *E. coli* plasmid-HBV recombinant (b) cleaving the resulting plasmid-HBV with Bam HI to produce a 1350 bp DNA fragment containing the $HB_sAg$ coding region (c) preparing recombinant plasmid-SV40 by ligating a Bam HI Eco RI digest of *E. coli* plasmid and SV40

(d) said 1350 bp DNA fragment is then ligated to Bam HI cleaved plasmid-SV40 to produce double recombinant *E. coli* plasmid-SV40-HBV (e) said double recombinant plasmid is then cleaved with Hae II to generate 4950 bp linear SV40-HBV recombinant molecules (f) infecting monkey kidney cells with the 4950 bp molecules and SV40 temperature sensitive early gene mutant helper virus and (g) culturing the infected cells to produce hepatitis B surface antigen.

2. The double recombinant plasmid produced by the process of claim 1 wherein the *E. coli* plasmid is pBR322.

* * * * *